United States Patent [19]

Schmidt et al.

[11] 4,381,303
[45] Apr. 26, 1983

[54] 1,4,9,10-TETRAHYDRO-PYRAZOLO [4,3-]PYRIDO[3,2-b][1,4]DIAZEPIN-10-ONES

[75] Inventors: Günther Schmidt; Wolfhard Engel; Wolfgang Eberlein, all of Biberach; Günter Trummlitz, Warthausen; Günther Engelhardt, Biberach, all of Fed. Rep. of Germany

[73] Assignee: Dr. Karl Thomae GmbH, Biberach an der Riss, Fed. Rep. of Germany

[21] Appl. No.: 377,911

[22] Filed: May 13, 1982

[30] Foreign Application Priority Data

Jun. 6, 1981 [DE] Fed. Rep. of Germany ....... 3122670

[51] Int. Cl.³ .................. A61K 31/55; C07D 471/14
[52] U.S. Cl. ........................... 424/252; 260/239.3 T; 546/278; 548/377
[58] Field of Search .............. 260/239.3 T; 424/252

[56] References Cited
U.S. PATENT DOCUMENTS 4,317,823  3/1982  Rainer .......................... 260/239.3 T Primary Examiner—Robert T. Bond
Attorney, Agent, or Firm—Hammond & Littell, Weissenberger & Muserlian

[57] ABSTRACT

This invention is directed to the compounds of the formula

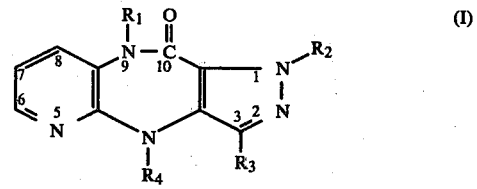

wherein
$R_1$ is hydrogen or an alkyl of from 1 to 6 carbon atoms;
$R_2$ is an alkyl of from 1 to 3 carbon atoms;
$R_3$ is hydrogen or an alkyl of from 1 to 3 carbon atoms; and
$R_4$ is hydrogen or an alkyl of from 1 to 4 carbon atoms.

These compounds are useful in pharmaceutical compositions which serve as analgesics, antiphlogistics and antipyretics.

30 Claims, No Drawings

1,4,9,10-TETRAHYDRO-PYRAZOLO [4,3-]PYRIDO[-3,2-b][1,4]DIAZEPIN-10-ONES

This invention relates to novel 1,4,9,10-tetrahydropyrazolo[4,3-e]pyrido[3,2-b][1,4]diazepin-10-ones, to processes for their preparation, to pharmaceutical compositions containing them as active ingredients, and to a method of using them as analgesics, antiphlogistics, and antipyretics.

More particularly, the present invention relates to compounds of the general formula

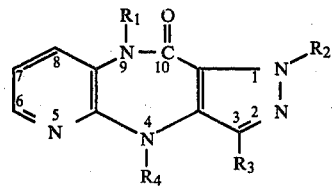

(I)

wherein
$R_1$ is hydrogen or an alkyl of from 1 to 6 carbon atoms;
$R_2$ is an alkyl of from 1 to 3 carbon atoms;
$R_3$ is hydrogen or an alkyl of from 1 to 3 carbon atoms; and
$R_4$ is hydrogen or an alkyl of from 1 to 4 carbon atoms.
Compounds of Formula I wherein
$R_1$ is hydrogen, methyl, ethyl, n-propyl, isopropyl, n-butyl, or isobutyl;
$R_2$ is methyl;
$R_3$ is hydrogen or methyl; and
$R_4$ is hydrogen or methyl, are preferred.

The compounds embraced by Formula I may be prepared by cyclizing an N-(2-halogen-3-pyridinyl)-4-amino-1H-pyrazole-5-carboxamide of the general formula

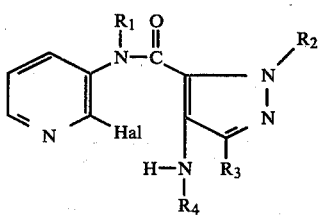

(II)

wherein $R_1$, $R_2$, $R_3$, and $R_4$ are as defined above and Hal represents a halogen, such as chlorine, bromine, or iodine, chlorine being preferred, while a hydrohalogenide is split off.

The cyclization is carried out in an organic solvent at temperatures of from about 80° to 200° C., preferably of from about 100° to 150° C. Suitable solvents include especially higher boiling solvents, such as sulfolane or 1,2,4-trichlorobenzene. The addition of catalytic amounts of a mineral acid such as sulfuric acid, hydrochloric acid, or phosphoric acid is advantageous for the cyclization reaction.

If, according to the invention, a compound of Formula I wherein $R_4$ is as defined above and $R_1$ represents a hydrogen is obtained, this can be converted by alkylation into a corresponding compound of Formula I wherein $R_4$ is as defined above and $R_1$ represents an alkyl of from 1 to 6 carbon atoms. If a compound of Formula I wherein $R_4$ represents an alkyl of from 1 to 6 carbon atoms and $R_4$ represents a hydrogen is obtained, this can be converted by alkylation into a corresponding compound of Formula I wherein $R_1$ represents an alkyl of from 1 to 6 carbon atoms and $R_4$ represents an alkyl of from 1 to 4 carbon atoms. If a compound of Formula I wherein $R_1$ and $R_4$ each represent hydrogen is obtained, this can be converted by alkylation into a corresponding compound of Formula I wherein $R_1$ and $R_4$ each represent an alkyl of from 1 to 4 carbon atoms.

The alkylation is carried out by, for example, use of dialkylsulfates or alkylhalogenides, preferably alkyliodides, in the presence of metalizing agents, such as sodium-amide or sodium hydride, and of a suitable solvent.

The starting compounds of Formula II can be prepared by reacting a 3-amino-2-halogen-pyridine of the general formula

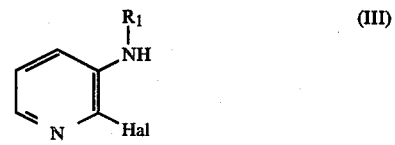

(III)

wherein $R_1$ and Hal are as defined above, with a 4-nitro-1H-pyrazole-5-carboxylic acid of the general formula

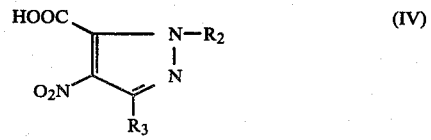

(IV)

wherein $R_2$ and $R_3$ are as defined above, either by means of thionyl chloride in a suitable solvent such as dioxane or hexamethylphosphoric acid triamide at temperatures of from about 60° to 90° C. or by means of phosphoroxide chloride and an organic base such as triethylamine with a suitable solvent such as toluene or dioxane at temperatures of from about 80° to 130° C. The resulting N-(2-halogen-3-pyridinyl)-4-nitro-1H-pyrazole-5-carboxamide of the general formula

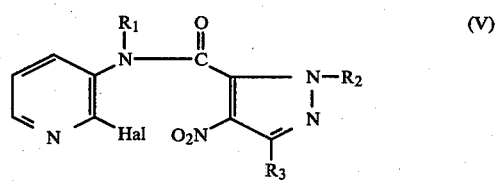

(V)

is then reduced to the starting compound of Formula II. The reduction of the nitro group to the amino group is carried out by, for example, hydrogenating a compound of Formula V in a suitable solvent such as, for example, dioxane, methanol, or ethanol, in the presence of a known hydrogenation catalyst, preferably Raney-Nickel, and at temperatures of from about 0° to 100° C. and a hydrogen pressure of from about 1 to 200 bar.

The compounds of general Formula I possess valuable pharmacological activities, in particular, analgesic, antiphlogistic, and antipyretic activities. Some of the compounds show, furthermore, a positive inotropic, diuretic and/or spasmolytic, sedative, muscle relaxing, and anxiolytic effect. Moreover, the compounds of Formula I wherein $R_1$ to $R_3$ are as defined above and $R_4$ represents hydrogen represent valuable intermediary products, for example, for the preparation of compounds of the present general Formula I wherein $R_1$ represents an alkyl of from 1 to 6 carbon atoms and/or $R_4$ represents an alkyl of from 1 to 4 carbon atoms. To demonstrate the advantageous pharmaceutical properties of the compounds of Formula I, the compounds A = 1,3-dimethyl-1,4,9,10-tetrahydro-pyrazolo[4,3-e]pyrido[3,2-b][1,4]diazepin-10-one, B = 1,4,9,10-tetrahydro-1,3,9-trimethyl-pyrazolo[4,3-e]pyrido[3,2-b][1,4]diazepin-10-one, C = 1,3-dimethyl-9-ethyl-1,4,9,10-tetrahydro-pyrazolo[4,3-e]pyrido[3,2-b][1,4]diazepin-10-one, D = 1,4,9,10-tetrahydro-1,3,4,9-tetramethyl-pyrazolo[4,3-e]pyrido[3,2-b][1,4]diazepin-10-one, E = 9-ethyl-1,4,9,10-tetrahydro-1,3,4-trimethyl-pyrazolo[4,3-e]pyrido[3,2-b][1,4]diazepin-10-one, and F = 9-(n-butyl)-1,3-dimethyl-1,4,9,10-tetrahydro-pyrazolo[4,3-e]pyrido[3,2-b][1,4]diazepin-10-one were tested with regard to analgesic activity in the rat, analgesic activity in the mouse, and acute toxicity in the mouse:

1. Activity against the Pain of Inflammation on the Back Paw of the Rat

The activity against the pain caused by inflammation was tested according to the method of RANDALL-SELITTO [Arch. Int. Pharmacodyn., 111, 409 (1957)]. Male Chbb:THOM-rats having body weights of from 100 to 130 grams received a subplantar injection of 0.1 ml of a suspension of 1,12 g of dry yeast in 18.9 ml of a 5.5% glucose solution into a back paw.

At 90 minutes after injection of the phlogistic, that is, ninety minutes before determination of the pain threshold, the animals received various doses of the test substances as a trituration in 1% methyl cellulose (1 ml/100 gm of animal) through an esophageal tube. Control animals received corresponding volumes of the vehicle. The pain threshold was determined in the rat in terms of the grams of bearing pressure on a paw, based on the weight of the animal.

From the pain threshold, measured according to the various doses of the test substance, and with linear regression analysis according to LINDER [Statistische Methoden, 4th ed., pp. 148-162, Birkhäuser, Basel, 1964] an $ED_{50}$ was determined. The $ED_{50}$ dose is one in which the pain threshold rises by 50%, as compared to the controls. The results are set forth in the following table:

TABLE 1

| Test Compound | $ED_{50}$ (mg/kg) |
|---|---|
| A | 26 |
| B | 11 |
| C | 28 |
| D | 7.4 |
| E | 5.9 |
| F | 139 |

2. Activity against the Sensitivity of the Mouse in the Hot Plate Test

The test was performed according to the method described by CHEN and BECKMAN [Science, 113, 631 (1951)] in male Chbb:NMRI (SPF)-mice with an average weight of 20 grams. The "hot plate" consisted of aluminum and had a temperature of 52° C. on its surface.

The test substances were administered as trituration in 1% methyl cellulose (0.1 ml/10 gm of mouse) by means of an esophageal tube. Before treatment with the test substances, the animals were twice put on the hot plate at intervals of 30 to 120 minutes, whereby their individual times of reaction were measured. After treatment with a test substance, the times of reaction of the animals were again measured in intervals of 30 to 120 minutes.

From the average maximum increase of the time of reaction obtained after treatment with different doses, and after linear regression analysis according to LINDER, an $ED_{100}$ dose was calculated. The $ED_{100}$ dose is one which increased the time of reaction by 100%. The results of the testing are set forth in the following table:

TABLE 2

| Test Compound | $ED_{100}$ (mg/kg) |
|---|---|
| A | 15 |
| B | 30 |
| C | 28 |
| F | 87 |

3. Acute Toxicity in Mice

The acute toxicity was determined in Chbb:NMRI (SPF)-mice of both sexes, having an average body weight of 20 grams. The test compounds were administered as a trituration in 1% methyl cellulose (0.2 ml/10 gm of animal) by means of an esophageal tube. The calculation of the $LD_{50}$ values was effected according to the method of LITCHFIELD and WILCOXON [J. Pharmacol. Exp. Ther., 96, 99 (1949)], based upon the percentage of animals which died within 14 days after administration of different doses. The results of the testing are set forth in the following table:

TABLE 3

| Test Compound | $LD_{50}$ (mg/kg) |
|---|---|
| A | 152 |
| B | 175 |
| C | 171 |
| D | 225 |
| E | 202 |
| F | >1000* |

*After administration of this dose, 1 out of 8 animals died.

Due to their pharmaceutical properties the compounds prepared according to the invention are suitable for use as active ingredients in pharmaceutical compositions with analgesic, antiphlogistic, and antipyretic activities. For pharmaceutical administration the compounds of general Formula I—optionally in combination with other active ingredients such as N-butyl-scopolaminiumbromide, codeine phosphate, amobarbital, acetylsalicyclic acid and/or caffeine—may be incorporated into the usual pharmaceutical preparations such as tablets, coated tablets, suppositories, capsules, or juices. The pharmaceutical compositions may comprise one or more of the compounds of Formula I as active ingredient as well as a pharmacologically acceptable carrier and/or other conventional additives. The single dose for adults may contain from about 10 to 200 mg (from about 0.1 to 2.7 mg/kg), preferably from about 50 to 100 mg (from about 0.7 to 1.3 mg/kg), of active ingredient, and the daily dose may contain from about 30 to 600 mg (from about 0.4 to 8 mg/kg), preferably from about 150 to 300 mg (from about 2 to 4 mg/kg), of active ingredient.

The following examples are intended to illustrate the invention and are not to be construed as limiting the invention thereto.

EXAMPLES

Preparation of the starting products:

EXAMPLE A

N-(2-Chloro-3-pyridinyl)-1,3-dimethyl-4-nitro-1H-pyrazole-5-carboxamide (a) An amount of 0.72 ml of thionyl chloride was added dropwise at room temperature to a suspension of 1.85 gm (0.01 mol) of 1,3-dimethyl-4-nitro-1H-pyrazole-5-carboxylic acid in 2 ml of hexamethylphosphoric acid triamide. After stirring for 20 minutes at 60° C., a solution of 1.28 gm (0.01 mol) of 2-chloro-3-aminopyridine in 2 ml of hexamethylphosphoric acid triamide was added dropwise to the above solution. After heating for 45 minutes up to 70° C., the reaction mixture was poured on ice, and the white crystals that precipitated were recovered by suction filtration, washed with water, stirred with dilute sodium bicarbonate solution, and subjected to suction filtration again. After drying, 2.3 gm (78% of theory) of the desired acid amide were obtained.

M.p.: 183°–185° C.

(b) The same substance was obtained according to the following method:

A solution of 0.52 ml of phosphoroxide chloride in 5 ml of toluene was added dropwise under reflux over a period of 60 minutes to a solution of 1.85 gm (0.01 mol) of 1,3-dimethyl-4-nitro-1H-pyrazole-5-carboxylic acid, 1.28 gm (0.01 mol) of 2-chloro-3-amino-pyridine, and 1.7 ml (0.01 mol) of triethylamine in 25 ml of toluene. After stirring for 90 minutes at 100° C., the solution was cooled, and 50 ml of water were added. The crystalline precipitate was recovered by suction filtration, stirred with dilute sodium bicarbonate solution, subjected to suction filtration again, and washed with water. An amount of 1.8 gm (60% of theory) of the desired acid amide was obtained.

M.p.: 183°–185° C.

EXAMPLE B

4-Amino-N-(2-chloro-3-pyridinyl)-1,3-dimethyl-1H-pyrazole-5-carboxamide

A quantity of 2.0 gm (0.0068 mol) of N-(2-chloro-3-pyridinyl)-1,3-dimethyl-4-nitro-1H-pyrazole-5-carboxamide was hydrogenated in 30 ml of dioxane with 0.7 gm of Raney-Nickel as catalyst at 70° C. and 30 bar. After the hydrogen absorption was finished, the catalyst was filtered off, and the dioxane was distilled off in vacuo. The crystalline residue was recrystallized from n-propanol. An amount of 1.3 gm (82% of theory) of the desired amino compound was obtained.

M.p.: 196°–198° C.

EXAMPLE C

N-(2-Chloro-3-pyridinyl)-4-(methylamino)-N,1,3-trimethyl-1H-pyrazole-5-carboxamide A mixture of 40.8 gm (0.091 mol) of N-(2-chloro-3-pyridinyl)-4-[[(4-methylphenyl)-sulfonyl]methylamino]-N,1,3-trimethyl-1H-pyrazole-5-carboxamide (prepared from N-(2-chloro-3-pyridinyl)-4-[[(4-methylphenyl)-sulfonyl]amino]-N,1,3-trimethyl-1H-pyrazole-5-carboxamide by reaction with sodium hydride in anhydrous N,N-dimethylformamide and subsequent reaction with methyl iodide) and 0.6 kg of polyphosphoric acid (content of phosphorpentoxide: 85%) was heated with stirring for 6 hours up to 60° C. The warm reaction mixture was stirred into cracked ice and subsequently mixed by means of external cooling with ice water with 40% aqueous sodium hydroxide solution until the precipitation was finished. After standing for 2 hours at +5° C., the strongly acidic reaction mixture was filtered off by suction filtration. The filtration residue was carefully washed with water and subsequently dried in the air. Yield: 20.9 gm (78% of theory).

EXAMPLE D

4-Amino-N-(2-chloro-3-pyridinyl)-1-methyl-1H-pyrazole-5-carboxamide (a) 1-Methyl-4-nitro-1H-pyrazole-5-carboxylic acid A quantity comprising 69.0 gm (0.547 mol) of 1-methyl-1H-pyrazole-5-carboxylic acid of m.p.: 227°–228° C. (R. Hüttel and M. E. Schön, Liebigs Ann. Chem 625, 55 [1959]) was added in small portions to a mixture of 200 ml of concentrated sulfuric acid and 60 ml of 90% fuming nitric acid under stirring. The temperature of the mixture rose from 75° C. at the beginning to a maximum temperature of 95° C. After the exothermal reaction was finished, heating was continued for 30 minutes up to 95° C. The cold mixture was stirred into 300 gm of cracked ice, and the resulting ice-cold suspension was filtered off by suction filtration. The filtration residue was washed with water, and after recrystallization from ethyl acetate, 44.0 gm (47% of theory) of pale yellow crystals were obtained.

M.p.: 169°–170° C. (decomp.).

(b) N-(2-Chloro-3-pyridinyl)-1-methyl-4-nitro-1H-pyrazole-5-carboxamide

Prepared analogously to Example A(a) from 1-methyl-4-nitro-1H-pyrazole-5-carboxylic acid, thionyl chloride, and 2-chloro-3-aminopyridine in hexamethylphosphoric acid triamide.

Yield: 86% of theory, M.p.: 150°–151° C.

(c) 4-Amino-N-(2-chloro-3-pyridinyl)-1-methyl-1H-pyrazole-5-caboxamide

A solution of 62.0 gm (0.22 mol) of N-(2-chloro-3-pyridinyl)-1-methyl-4-nitro-1H-pyrazole-5-carboxamide in 1 liter of dioxane was hydrogenated in the presence of 5 gm of 10% palladium/animal charcoal as catalyst at room temperature and 5 bar until the hydrogen absorption was finished. After removal of the catalyst and the resulting precipitate by filtration, the filtrate was evaporated in vacuo. The remaining distillation residue was recrystallized from methanol.

Yield: 25.0 gm (45% of theory) of colorless crystals, M.p.: 124°–125° C.

Preparation of end products:

EXAMPLE 1

1,3-Dimethyl-1,4,9,10-tetrahydro-pyrazolo[4,3-e]pyrido[3,2-b][1,4]diazepin-10-one Quantities of 25.7 gm (0.0966 mol) of 4-amino-N-(2-chloro-3-pyridinyl)-1,3-dimethyl-1H-pyrazole-5-carboxamide and 0.5 ml of concentrated sulfuric acid were stirred in 50 ml of solfolane for 2.5 hours at 130° C. After cooling, the crystal slurry was recovered by suction filtration and washed with n-propanol. The crystals obtained were stirred with dilute aqueous ammonia and subjected to suction filtration.

Yield: 21.3 gm (96% of theory), M.p.: 197°–199° C. (from ethyl acetate).

EXAMPLE 2

1,4,9,10-Tetrahydro-1,3,9-trimethyl-pyrazolo[4,3-e]pyrido-[3,2-b][1,4]diazepin-10one An amount of 5.25 gm (0.025 mol) of 1,3-dimethyl-1,4,9,10-tetrahydro-pyrazolo[4,3-e]pyrido[3,2-b][1,4]diazepin-10-one was dissolved in 25 ml of N,N-dimethylformamide and mixed with 1.2 gm of a 55% sodium hydride dispersion in mineral oil. After stirring for 2 hours at 60° C., the solution was cooled to 40° C., and 2.2 ml of methyl iodide were added dropwise. Subsequently the mixture was stirred for 3 hours at 40° C., and after addition of 50 ml of water and cooling in the ice-bath, the desired compound was obtained in crystals. The crystals were recovered by suction filtration, and the mineral oil was washed out by means of petroleum ether.

Yield: 3.0 gm (50% of theory), M.p.: 141°–141.5° C. (from aqueous ethanol).

EXAMPLE 3

1,3-Dimethyl-9-ethyl-1,4,9,10-tetrahydro-pyrazolo[4,3-e]pyrido[3,2-b][1,4]diazepin-10-one The preparation was carried out analogously to Example 2 from 1,3-dimethyl-1,4,9,10-tetrahydro-pyrazolo[4,3-e]pyrido[3,2-b][1,4]diazepin-10-one, sodium hydride, and ethyl iodide in N,N-dimethylformamide. The crude product was purified by column chromatography (silica gel; eluant: methylene chloride/ethyl acetate (4:1)).

Yield: 62% of theory, (M.p.: 137°–138° C. (from aqueous ethanol).

EXAMPLE 4

1,4,9,10-Tetrahydro-1,3,4,9-tetramethyl-pyrazolo[4,3-e]pyrido[3,2-b][1,4]diazepin-10-one An amount of 4.6 gm (0.02 mol) of 1,3-dimethyl-1,4,9,10-tetrahydro-pyrazolo[4,3-d]pyrido[3,2-b][1,4]diazepin-10-one was dissolved in 20 ml of N,N-dimethylformamide, mixed with 2.2 gm of a 55% sodium hydride dispersion in mineral oil, and stirred for 30 minutes at 60° C. After cooling to 40° C., 3.7 ml of methyl iodide were added thereto dropwise, and the reaction mixture was stirred for a further 2 hours at 40° C. The resulting crystal slurry was mixed with 50 ml of water, cooled to 0° C. in an ice bath, and subjected to suction filtration. After recrystallization from aqueous ethanol, 3 gm of the desired compound was obtained (59% of theory).

M.p.: 147°–148.5° C.

EXAMPLE 5

1,4,9,10-Tetrahydro-1,3,4,9-tetramethyl-pyrazolo[4,3-e]pyrido[3,2-b][1,4]diazepin-10-one An amount of 5.9 gm of N-(2-chloro-3-pyridinyl)-N-methyl-1,3-dimethyl-4-methylamino-1H-pyrazole-5-carboxamide was stirred in 6 ml of 1,2,4-trichlorobenzene for 5 hours at 180° C. After cooling, the crystal slurry was subjected to suction filtration, washed with cyclohexane, and recrystallized from aqueous ethanol.

Yield: 74% of theory, M.p.: 147°–148.5° C.

EXAMPLE 6

9-Ethyl-1,4,9,10-tetrahydro-1,3,4-trimethyl-pyrazolo[4,3-e]-pyrido[3,2-b][1,4]diazepin-10one An amount of 6.0 gm of 1,3-dimethyl-9-ethyl-1,4,9,10-tetrahydro-pyrazolo[4,3-e]pyrido[3,2-b][diazepin-10-one was dissolved in 30 ml of N,N-dimethylformamide, mixed with 1.1 gm of a 55% sodium hydride dispersion in mineral oil, and stirred for 2 hours at 60° C. After cooling to 40° C., 1.9 ml of methyl iodide were added thereto dropwise, and the mixture was stirred for 2 hours at 40° C. The reaction mixture was evaporated in vacuo, and the residue was purified by column chromatography (silica gel; eluant: methylene chloride/ethyl acetate (11:5)).

Yield: 75% of theory, M.p.: 127°–129° C. (from aqueous ethanol).

EXAMPLE 7

9-(n-Butyl)-1,3-dimethyl-1,4,9,10-tetrahydro-pyrazolo[4,3-e]pyrido[3,2-b][1,4]diazepin-10-one The preparation was carried out analogously to Example 3 from 1,3-dimethyl-1,4,9,10-tetrahydro-pyrazolo[4,3-e]pyrido[3,2-b][1,4]diazepin-10-one, sodium hydride, and n-butyl bromide in N,N-dimethylformamide with subsequent chromatographic purification.

Yield: 67% of theory, M.p.: 144°–146° C. (from ethyl acetate).

EXAMPLE 8

9-(n-Butyl)-1,4,9,10-tetrahydro-1,3,4-trimethyl-pyrazolo[4,3-e]pyrido[3,2-b][1,4]diazepin-10-one Prepared analogously to Example 6 from 9-(n-butyl)-1,3-dimethyl-1,4,9,10-tetrahydro-pyrazolo[4,3-e]pyrido[3,2-b][1,4]diazepin-10-one, sodium hydride, and methyl iodide in N,N-dimethylformamide with subsequent chromatographic purification.

Yield: 61% of theory, M.p.: 93°–93.5° C. (from petroleum ether).

EXAMPLE 9

1-Methyl-1,4,9,10-tetrahydro-pyrazolo[4,3-e]pyrido[3,2-b][1,4]diazepin-10-one An amount of 25.0 gm (0.099 mol) of 4-amino-N-(2-chloro-3-pyridinyl)-1-methyl-1H-pyrazole-5-carboxamide was dissolved in 100 ml of sulfolane and, after addition of 5 drops of concentrated sulfuric acid, heated for 1 hour to 120° C. The cold reaction mixture was filtered, and the filtration residue was suspended with 5% aqueous ammonia solution and again filtered. The product obtained was thoroughly washed with water, stirred with methanol, and subjected to cold suction filtration. After drying, 14.6 gm (68.5% of theory) of colorless crystals were obtained (m.p.: 304°–305° C.).

EXAMPLE 10

1,3-Dimethyl-9-(n-propyl)-1,4,9,10-tetrahydro-pyrazolo[4,3-e]pyrido[3,2-b][1,4]diazepin-10-one Prepared analogously to Example 2 from 1,3-dimethyl-1,4,9,10-tetrahydro-pyrazolo[4,3-e]pyrido[3,2-b][1,4]diazepin-10-one, sodium hydride, and n-propyl bromide in N,N-dimethylformamide with subsequent chromatographic purification (silica gel; eluant: methylene chloride/ethyl acetate (4:1)).

Yield: 61% of theory, M.p.: 196°–197.5° C. (from ethyl acetate).

EXAMPLE 11

1,3-Dimethyl-9-isopropyl-1,4,9,10-tetrahydro-pyrazolo[4,3-e]pyrido[3,2-b][1,4]diazepin-10-one Prepared analogously to Example 2 from 1,3-dimethyl-1,4,9,10-tetrahydro-pyrazolo[4,3-e]pyrido[3,2-b][1,4]diazepin-10-one, sodium hydride, and isopropyl bromide in N,N-dimethylformamide with subsequent chromatographic purification (silica gel; eluant: methylene chloride/ethyl acetate (4:1)).

Yield: 56% of theory, M.p.: 155°–157° C. (from ethyl acetate).

EXAMPLE 12

1,3-Dimethyl-9-isobutyl-1,4,9,10-tetrahydro-pyrazolo-[4,3-e]pyrido[3,2-b][1,4]diazepin-10-one Prepared analogously to Example 2 from 1,3-dimethyl-1,4,9,10-tetrahydro-pyrazolo[4,3]pyrido[3,2-b][1,4]diazepin-10-one, sodium hydride, and isobutyl bromide in N,N-dimethylformamide with subsequent chromatographic purification (silica gel; eluant: methylene chloride/ethyl acetate (4:1)).

Yield: 63% of theory, M.p.: 180°–182° C. (from ethyl acetate).

The following examples are intended to illustrate the product of some pharmaceutical preparations according to the invention. As would be appreciated by those skilled in the art, any one of the compounds of general Formula I, or a mixture thereof, could be used as active ingredient in these preparations.

EXAMPLE 13

Tablets containing 50 mg of 1,4,9,10-tetrahydro-1,3,9-trimethyl-pyrazolo[4,3-e]pyrido[3,2-b][1,4]-diazepin-10-one Composition of one tablet:

| Component | Amount (mg) |
| --- | --- |
| Active ingredient | 50.0 |
| Lactose | 128.0 |
| Potato starch | 40.0 |
| Magnesium stearate | 2.0 |
| | 220.0 |

Method of preparation:

A 10% mucus was prepared from the potato starch by heating. The active ingredient, the lactose, and the remaining potato starch were mixed, and together with the mucus the mixture was granulated through a screen of mesh size 1.5 mm. The granulate was dried at 45° C., granulated again through the above-mentioned screen, mixed with magnesium stearate, and pressed into tablets.

Weight of tablets: 220 mg
Punch: 9 mm

EXAMPLE 14

Coated tablets containing 50 mg of 1,4,9,10-tetrahydro-1,3,9-trimethyl-pyrazolo[4,3-e]pyrido[3,2-b][1,4]diazepin-10-one The tablets prepared according to Example 13 were covered with a coating in conventional manner, which coating consisted essentially of sugar and talcum. The finished coated tablets were polished by means of bees wax.

Weight of coated tablets: 300 mg

EXAMPLE 15

Suppositories containing 70 mg of 1,4,9,10-tetrahydro-1,3,9-trimethyl-pyrazolo[4,3-e]pyrido[3,2-b][1,4]diazepin-10-one Composition of one suppository:

| Component | Amount (mg) |
| --- | --- |
| Active ingredient | 70.0 |
| Suppository mass (e.g., cocoa butter or Witepsol W 45 ®, available from Fa. Chemische Werke Witten GmbH) | 1630.0 |
| | 1700.0 |

Method of preparation:

Finely powdered active ingredient was suspended in melted supossitory mass, which suspension was cooled to 40° C. The mass was poured at 37° C. into slightly pre-cooled suppository forms.

Weight of suppositories: 1.7 gm

The preceding specific embodiments are illustrative of the practice of the invention. It is to be understood, however, that other expedients known to those skilled in the are or disclosed herein, may be employed without departing from the spirit of the invention or the scope of the appended claims.

We claim:

1. A compound of the formula

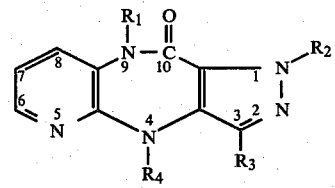

wherein $R_1$ is hydrogen or an alkyl of from 1 to 6 carbon atoms;

$R_2$ is an alkyl of from 1 to 3 carbon atoms;

$R_3$ is hydrogen or an alkyl of from 1 to 3 carbon atoms; and $R_4$ is hydrogen or an alkyl of from 1 to 4 carbon atoms.

2. A compound of claim 1, wherein $R_1$ is hydrogen or an alkyl of from 1 to 3 carbon atoms;

$R_2$ is an alkyl of from 1 to 3 carbon atoms;

$R_3$ is hydrogen or an alkyl of from 1 to 3 carbon atoms; and $R_4$ is hydrogen.

3. A compound of claim 1, wherein $R_1$ is hydrogen, methyl, ethyl, n-propyl, isopropyl, n-butyl, or isobutyl;

$R_2$ is methyl;

$R_3$ is hydrogen or methyl; and $R_4$ is hydrogen or methyl.

4. The compound of claim 1 which is 1,3-dimethyl-1,4,9,10-tetrahydro-pyrazolo[4,3-e]pyrido[3,2-b][1,4]diazepin-10-one.

5. The compound of claim 1 which is 1,4,9,10-tetrahydro-1,3,9-trimethyl-pyrazolo[4,3-e]pyrido[3,2-b][1,4]diazepin-10-one.

6. The compound of claim 1 which is 1,3-dimethyl-9-ethyl-1,4,9,10-tetrahydro-pyrazolo[4,3-e]pyrido[3,2-b][1,4]diazepin-10-one.

7. The compound of claim 1 which is 1,4,9,10-tetrahydro-1,3,4,9-tetramethyl-pyrazolo[4,3-e]pyrido[3,2-b][1,4]diazepin-10-one.

8. The compound of claim 1 which is 9-ethyl-1,4,9,10-tetrahydro-1,3,4-trimethyl-pyrazolo[4,3-e]pyrido[3,2-b][1,4]-diazepin-10-one.

9. The compound of claim 1 which is 9-(n-butyl)-1,3-dimethyl-1,4,9,10-tetrahydro-pyrazolo[4,3-e]pyrido[3,2-b][1,4]-diazepin-10-one.

10. A pharmaceutical composition for relieving pain comprising as an active ingredient a pain relieving effective amount of at least one compound of claim 1 and a pharmacologically acceptable carrier.

11. The pharmaceutical composition of claim 10, wherein a single dose for adults comprises from about 10 to 200 mg of active ingredient.

12. The pharmaceutical composition of claim 11, wherein a single dose comprises from about 50 to 100 mg of active ingredient.

13. The pharmaceutical composition of claim 10, wherein a compound of claim 1 is the sole active ingredient.

14. The pharmaceutical composition of claim 10, wherein the active ingredient is 1,3-dimethyl-1,4,9,10-tetrahydropyrazolo[4,3-e]pyrido[3,2-b][1,4]diazepin-10-one.

15. The pharmaceutical composition of claim 10, wherein the active ingredient is 1,4,9,10-tetrahydro-1,3,9-trimethyl-pyrazolo[4,3-e]pyrido[3,2-b][1,4]diazepin-10-one.

16. The pharmaceutical composition of claim 10, wherein the active ingredient is 1,3-dimethyl-9-ethyl-1,4,9,10-tetrahydro-pyrazolo[4,3-e]pyrido[3,2-b][1,4]diazepin-10-one.

17. The pharmaceutical composition of claim 10, wherein the active ingredient is 1,4,9,10-tetrahydro-1,3,4,9-tetramethyl-pyrazolo[4,3-e]pyrido[3,2-b][1,4]diazepin-10-one.

18. The pharmaceutical composition of claim 10, wherein the active ingredient is 9-ethyl-1,4,9,10-tetrahydro-1,3,4-trimethyl-pyrazolo[4,3-e]pyrido[3,2-b][1,4]diazepin-10-one.

19. The pharmaceutical composition of claim 10, wherein the active ingredient is 9-(n-butyl)-1,3-dimethyl-1,4,9,10-tetrahydro-pyrazolo[4,3-e]pyrido[3,2-b][1,4]diazepin-10-one.

20. A method of inducing analgesic, antiphlogistic and antipyretic activity in a host which comprises administering to a host in need of such treatment an analgesically effective amount of active ingredient comprising at least one compound of claim 1.

21. The method of claim 20, wherein a single dose comprising from about 10 to 200 mg of active ingredient is administered to an adult.

22. The method of claim 21, wherein a single dose comprising from about 50 to 100 mg of active ingredient is administered.

23. The method of claim 20, wherein from about 30 to 600 mg of active ingredient are administered daily.

24. The method of claim 23, wherein from about 150 to 300 mg of active ingredient are administered daily.

25. The method of claim 20, wherein the active ingredient is 1,3-dimethyl-1,4,9,10-tetrahydro-pyrazolo[4,3-e]pyrido[3,2-b][1,4]diazepin-10-one.

26. The method of claim 20, wherein the active ingredient is 1,4,9,10-tetrahydro-1,3,9-trimethyl-pyrazolo[4,3-e]pyrido[3,2-b][1,4]diazepin-10-one.

27. The method of claim 20, wherein the active ingredient is 1,3-dimethyl-9-ethyl-1,4,9,10-tetrahydro-pyrazolo-[4,3-e]pyrido[3,2-b][1,4]diazepin-10-one.

28. The method of claim 20, wherein the active ingredient is 1,4,9,10-tetrahydro-1,3,4,9-tetramethyl-pyrazolo[4,3-e]pyrido[3,2-b][1,4]diazepin-10-one.

29. The method of claim 20, wherein the active ingredient is 9-ethyl-1,4,9,10-tetrahydro-1,3,4-trimethyl-pyrazolo[4,3-e]pyrido[3,2-b][1,4]diazepin-10-one.

30. The method of claim 20, wherein the active ingredient is 9-(n-butyl)-1,3-dimethyl-tetrahydro-pyrazolo[4,3-e]pyrido[3,2-b][1,4]diazepin-10-one.

* * * * *

UNITED STATES PATENT AND TRADEMARK OFFICE
CERTIFICATE OF CORRECTION

PATENT NO. : 4,381,303
DATED     : April 26, 1983
INVENTOR(S) : GÜNTHER SCHMIDT ET AL.

It is certified that error appears in the above-identified patent and that said Letters Patent is hereby corrected as shown below:

Title page [54]; and Column 1: In the title "[4,3-]" should read -- [4,3-e] --.

Column 7, line 4 and Column 8, line 4: "10one" should read -- 10-one --.

Column 9, line 19: "[4,3]" should read -- [4,3-e] --.

Signed and Sealed this

Fifth Day of July 1983

[SEAL]

Attest:

GERALD J. MOSSINGHOFF

Attesting Officer                Commissioner of Patents and Trademarks